United States Patent [19]

Pillai et al.

[11] Patent Number: 5,334,379
[45] Date of Patent: Aug. 2, 1994

[54] CYTOKINE AND HORMONE CARRIERS FOR CONJUGATE VACCINES

[75] Inventors: Subramonia Pillai; Ronald Eby, both of Rochester, N.Y.

[73] Assignee: American Cyanamid Company, Wayne, N.J.

[21] Appl. No.: 553,901

[22] Filed: Jul. 16, 1990

Related U.S. Application Data

[63] Continuation-in-part of Ser. No. 380,566, Jul. 14, 1989.

[51] Int. Cl.$^5$ .............. A61K 37/66; A61K 39/02; A61K 39/385; C07K 15/26

[52] U.S. Cl. .................. 424/85.2; 424/85.1; 424/85.4; 424/197.11; 424/244.1; 424/250.1; 424/831; 530/351; 530/395; 530/404; 530/405; 530/406; 530/411

[58] Field of Search ............... 530/351, 303, 395, 399, 530/403, 404, 405, 806, 807, 411; 424/85.1, 85.2, 85.4, 88, 89, 90, 91, 92

[56] References Cited

U.S. PATENT DOCUMENTS

| | | | |
|---|---|---|---|
| 4,673,574 | 6/1987 | Anderson | 424/92 |
| 4,675,382 | 6/1987 | Murphy | 530/350 |
| 4,695,624 | 9/1987 | Marburg et al. | 530/395 |
| 4,745,180 | 5/1988 | Moreland et al. | 530/351 |
| 4,761,283 | 8/1988 | Anderson | 424/92 |
| 4,766,106 | 8/1988 | Katre et al. | 514/12 |
| 4,772,685 | 9/1988 | Schmidt et al. | 530/326 |
| 4,801,575 | 1/1989 | Pardridge | 514/4 |
| 4,820,514 | 4/1989 | Cummins | 424/85.4 |
| 4,902,505 | 2/1990 | Pardridge et al. | 424/85.4 |
| 4,935,233 | 6/1990 | Bell et al. | 424/85.5 |
| 4,946,945 | 8/1990 | Wojdam | 530/402 |
| 4,962,188 | 10/1990 | Frankel | 530/389 |
| 4,987,237 | 1/1991 | Myers et al. | 549/202 |
| 5,013,824 | 5/1991 | Abrams et al. | 530/351 |
| 5,039,790 | 8/1991 | Adams et al. | 530/324 |
| 5,073,627 | 12/1991 | Curtis et al. | 530/351 |

FOREIGN PATENT DOCUMENTS

| | | |
|---|---|---|
| 0141484 | 5/1985 | European Pat. Off. |
| 0158198 | 10/1985 | European Pat. Off. |
| 183503 | 6/1986 | European Pat. Off. |
| WO87/00056 | 1/1987 | World Int. Prop. O. |
| WO88/00971 | 2/1988 | World Int. Prop. O. |

OTHER PUBLICATIONS

Abstract of Sorenden et al. (1984) Acta Pathol. Microbiol. Immunol. Scand. 92(6):35-6.
Abstract of Slaghek et al. (1991) Carbohydrate Res. 211(1) 25-39.
Wassels et al. (1987) Proc. Natl. Acad. Sci. U.S.A. 84:9170-9174 "A Model of High-Affinity Antibody Binding to Type III Group B Streptococcus Capsular Polysaccharide".
Pillar et al. (1991) Infect. Immunity 59 (12):4371-4376 "Distinct Pattern of Antibody Raretivity with Oligomers of Polymeric Forms . . . " *Bacterial Cell Surface Techniques* Hancock et al. pp. 17 and 7.
*Practical Handbook of Microbiology* ed O'Leary CRC Press, Inc. Boca Raton, Fl. pp. 405-407 definition of endotoxin (LPS).
*Current Topics in Microbiology* 150 and Immunology: Bacterial Capsules ed. by Jann et al. pp. 1-2 "Genetics of Capsular Polyacchande Production" by Boulnois et al.
Anderson (1984) J. Infectious Dis. 149(6): 1034.
Kayhty et al. (1986) J. Infect. Dis. 149 (6):1034-1035.
Kayhty et al. (1983) J. Infect. Dis. 147(6):1100.
Makela et al. (1977) J. Infect. Dis 136 (Suppl):543-550.
Ambrosino et al. (1983) Infect. Immunity 39(2):709-714.
*Attorneys Dictionary of Medicine and Word Finder* J. E. Schmidt, vol. 1 p. A-107; vol. 4 p. V-36 Matthew Bender & Co., Inc. 1991.
Nencioni et al. (1987) J. Immunology 139 (3):800-804.
Chaudhary et al. (1987) PNAS U.S.A. 84:4538-42.
Lorberboum-Galski et al. (1988) PNAS U.S.A. 85:1922-1926.

*Primary Examiner*—Kay K. Kim
*Attorney, Agent, or Firm*—Estelle J. Tsevdos

[57] ABSTRACT

This invention pertains to immunogenic conjugates comprising a carbohydrate containing antigen or other antigen bound to or genetically fused with a cytokine, lymphokine, hormone or growth factor having immunomodulating activity, wherein the cytokine, lymphokine, hormone or growth factor is capable of modifying immunogenicity of the carbohydrate containing antigen. The cytokine or lymphokine can be an interleukin or an interferon. The immunogenic conjugate can be used in vaccine and co-vaccine formulations.

17 Claims, 8 Drawing Sheets

| 1 | 2 | 3 | 4 | 5 | 6 | 7 | 8 |
|---|---|---|---|---|---|---|---|
| o |   |   | • | • |   | o | o |

1. PRP-CRM            2. IL-2 only
3. PRP only           4. PRP-IL-2 (2X)
5. PRP-IL-2 (2X)      6. —
7. PRP-IL-2 (20X)     8. PRP-IL-2 (20X)

1 2 3 4 5 6 7 8 9 10

Probed with monoclonal anti-PRP

1) Blank
2) Low molecular weight marker
3) Bovine rIL-2
4) PRP-IL-2 (20:1)
5) PRP-IL-2 (2:1)

Probed with polyclonal rabbit anti-BrIL-2

6) Low molecular weight marker
7) Bovine rIL-2
8) PRP-IL-2 (20:1)
9) PRP-IL-2 (2:1)
10) Blank

CYTOKINE AND HORMONE CARRIERS FOR CONJUGATE VACCINES

RELATED APPLICATION

This is a continuation-in-part application of U.S. Ser. No. 07/380 566 filed Jul. 14, 1989 the contents of which are hereby incorporated by reference.

BACKGROUND OF THE ART

Cytokines and lymphokines, such as interferons, GM-CSF, IL-1, IL-2, IL-3, IL-4, IL-5, IL-6 and IL-7 have been shown to have different activities in modulating the immune response. Hormones and growth factors also have modulating effects on cells of the immune system and thus can modulate the immune response. Interferons, IL-1 and IL-2 augment proliferation and differentiation of antigen or mitogen stimulated T cells. They also stimulate B cells to grow and generate antibody responses to anti gels once activated, B cells have been shown to express IL-2 receptors. A number of synthetic and recombinant lymphokines (Nencioni et al., *J. Immunol.* 139:800–804 (1987); Kronheim et al., U.S. Pat. No. 4,801,686; Tagliabue et al., U.S. Pat. No. 4,774,320; Fernandes et al., U.S. Pat. No. 4,604,377) have been shown to stimulate immune functions. However, inflammatory and toxic effects often accompany immunotherapeutic administration of cytokines or lymphokines to an organism. In addition, these molecules generally have short half lives.

Certain cytokines and lymphokines have been shown to have adjuvant activity thereby enhancing immune response to an antigen. For example, Nakamura et al. demonstrated that interferon-gamma induced a two- to five-fold enhancement of antibody formation to several antigens. Nakamura et al., *Nature* 307:381–382 (1984). Interleukins have also been shown to enhance an immune response to antigens. Nencioni et al., *J. Immunol.* 139:800–804 (1987); Howard et al., EP285441.

The stimulation of antibody response to poorly immunogenic thymus-independent antigens such as polysaccharides has been accomplished in recent years by the covalent coupling of polysaccharides onto a strong thymus-dependent protein antigen. A number of proteins such as diphtheria toxoid, tetanus toxoid and a non-toxic variant of diphtheria toxin, $CRM_{197}$ are used as carriers for polysaccharides. The immune response is highly variable depending on the type of protein used as carrier.

A number of conjugates have been previously described for stabilizing and solubilizing proteins such as lymphokines. Moreland and Nitecki (U.S. Pat. No. 4,745,180 May 17, 1988) describe a pharmaceutical composition comprising $\beta$-interferon interleukin-2 or an immunotoxin which is covalently conjugated to a heparin fragment. The conjugate provides a means for solubilizing the protein which is essentially insoluble in its unconjugated form.

Schmidt et al. (U.S. Pat. No. 4,772,685, Sep. 20, 1988) describe immunogenic conjugates of IL-1 derived peptides to a high molecular weight carrier protein. Conjugates of IL-2 or interferon and a water soluble polymer (polyethylene glycol) have been described (Katre and Knauf, U.S. Pat. No. 4,766,106, Aug. 23, 1988 and WO8700056 Jan. 15, 1987). Similarly, Carman (EP183503 Jun. 4, 1986) describes conjugates of interferon or IL-2 linked to a water soluble polymer for sustained release of the lymphokine. For background on hormones and growth factors and their receptors see, for example, Hill, D. J., *J. Reprod, Fertility* 85: 723–734 (1989); Roupas et al., *Mol. Cell. Endocrinol.* 61:1–12 (1989).

SUMMARY OF THE INVENTION

This invention pertains to immunogenic conjugates and vaccine compositions containing the immunogenic conjugate. The conjugates comprise an antigen (not normally associated with the cytokine, lymphokine, hormone or growth factor), especially a carbohydrate containing antigen, bound to a cytokine, lymphokine, hormone or growth factor having immunomodulating activity, wherein the cytokine, lymphokine, hormone or growth factor modifies the immunogenic activity of the antigen. The cytokine or lymphokine can be an interleukin, such as interleukin-1$\alpha$, interleukin-1$\beta$, interleukin-2, an interferon, such as interferon gamma, or other cytokine or lymphokine which has immunomodulating activity. The hormone or growth factor can be of bovine, porcine or chicken origin, for example, and can be tumor RS necrosis factor (TNF), prolactin, epidermal growth factor (EGF), tissue growth factor (TGF), granulocyte macrophage colony stimulating factor (GMCSF), granulocyte colony stimulating factor (GCSF), insulin-like growth factor (IGF-1), somatotropin or insulin, or any other hormone or growth factor whose receptor is expressed on cells of the immune system.

The invention further pertains to a method for eliciting an immune response which comprises administering to an animal an immunogenic amount of a vaccine composition comprising the immunogenic conjugate of the present invention in a pharmaceutically acceptable vehicle and an optional adjuvant. The immunogenic conjugate can be admixed with a coadministered antigen which may be a conjugate, complex or mixture from the same or a different organism than that from which the antigen is derived, in a pharmaceutically acceptable vehicle and an optional adjuvant to produce a co-vaccine which can be used to elicit an immune response to both the conjugated antigen and the admixed antigen.

Figure 1:
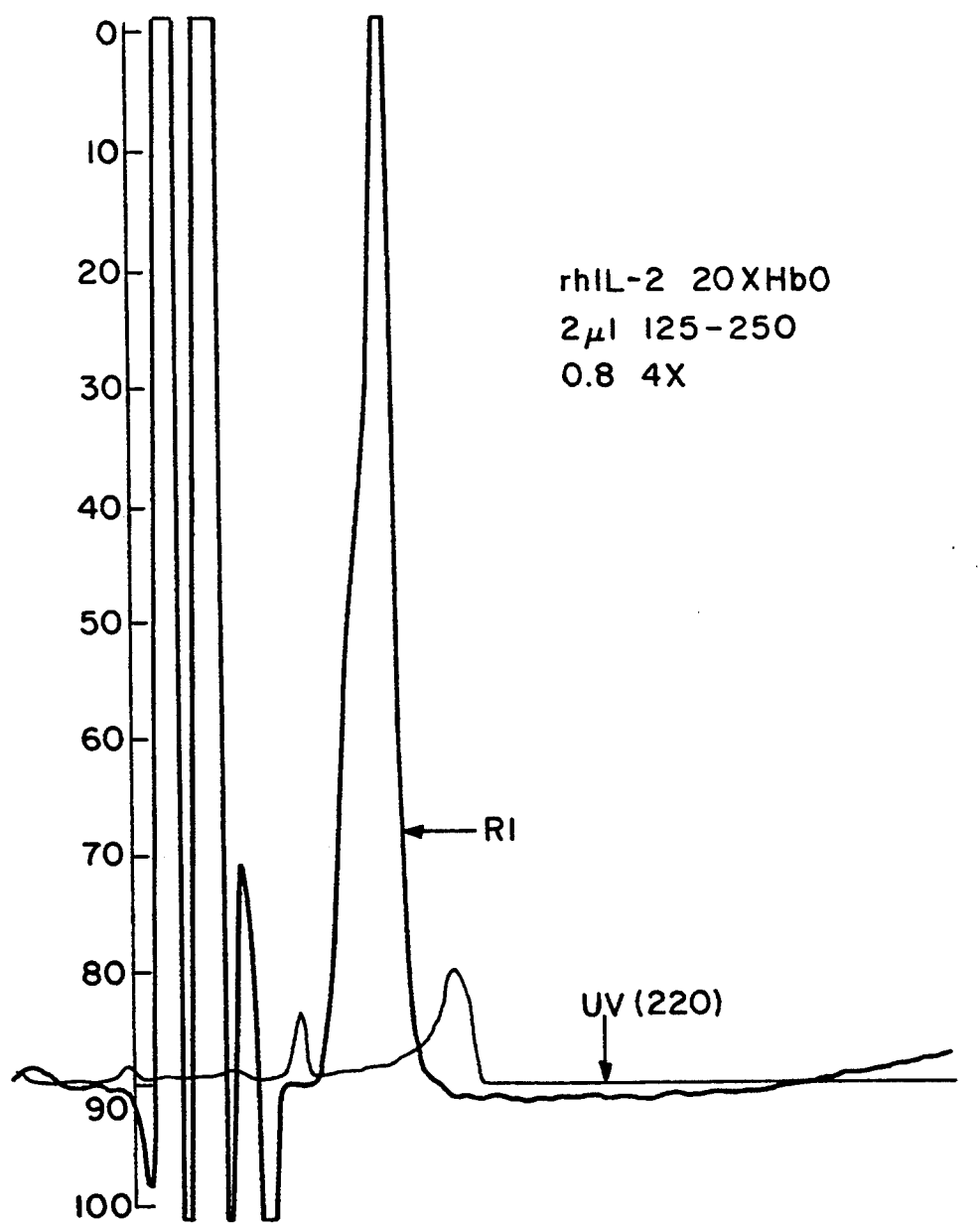
FIG. 1 shows high pressure liquid chromatographic (HPLC) analysis of unconjugated recombinant human IL-2 (rhIL-2) compared to crude polyribosylribitol-phosphate(PRF)-rhIL-2 conjugates.

DETAILED DESCRIPTION OF THE INVENTION

This invention pertains to immunogenic conjugates comprising an antigen, particularly a protein, a peptide, an oligo- or polysaccharide or other carbohydrate containing antigen bound to a cytokine, lymphokine, hormone or growth factor. The conjugation of the antigen to the cytokine, lymphokine, hormone or growth factor provides an immunogenic conjugate which can modify the immune response to the antigen. In addition to modified immunogenicity, the antigenic component of the conjugate can stabilize the cytokine, lymphokine, hormone or growth factor.

The cytokine, lymphokine, hormone or growth factor functions to modulate the immune response to the antigen and the latter stabilizes the biological activity of the cytokine, lymphokine, hormone or growth factor. The cytokine, lymphokine, hormone or growth factor can be an interleukin such as interleukin-1$\alpha$, interleukin-1$\beta$, interleukin-2, an interferon, such as interferon gamma, or other cytokine or lymphokine which has immunomodulating activity. Portions of cytokines or lymphokines or muteins or mimics having immunomodulating activity can also be used. Preferably, the lymphokine is interleukin-2. The hormone, growth factor or immunomodulating portions thereof can be of bovine, porcine or chicken origin, for example, and can be tumor necrosis factor (TNF), prolactin, epidermal growth factor (EGF), tissue growth factor (TGF), granulocyte macrophage colony stimulating factor (GMCSF), granulocyte colony stimulating factor (GCSF), insulin-like growth factor (IGF-1), somatotropin (growth hormone) or insulin, or any other hormone or growth factor whose receptor is expressed on cells of the immune system.

Cytokines, lymphokines, hormones or growth factors can be obtained from any suitable source. They can be produced by recombinant DNA methodology. For example, the genes encoding several human interleukins have been cloned and expressed in a variety of host systems, permitting the production of large quantities of pure human interleukin. Further, certain T lymphocyte lines produce high levels of interleukin, thus providing a source of the lymphokine.

The carbohydrate containing antigen or non-carbohydrate antigen can be derived from any source to which an immunogenic response is desired. The carbohydrate containing antigen or other antigen can be one which is not itself immunogenic or weakly so, but can become immunogenic or more so by virtue of conjugation to the cytokine, lymphokine, hormone or growth factor. The carbohydrate containing antigen can be an oligosaccharide, polysaccharide, peptidoglycan and glycopeptide. Examples of carbohydrate containing antigens of interest include bacterial capsular polymers, lipopolysaccharide or lipopolysaccharide components, auto-immunity related antigens, allergens, tumor-associated antigens, fungal and vital antigens, hormones and bacterial cell wall components, such as peptidoglycans or fragments thereof.

Bacterial capsular polymers, oligomers and fragments thereof are among the groups of antigens which have potential to be effectively employed in a vaccine but which are only weakly immunogenic in young humans. As used in this application, the term "capsular polymers" refers to sugar-containing polymers, such as polymers of sugars, sugar acids, amino sugars, and sugar phosphates. These "capsular polymers" are frequently referred to in the medical literature as "capsular polysaccharides" though they may contain linkages other than glycosidic linkages and constituents other than sugars such as those listed above.

The capsular polymers (CP) can be derived from many different types of bacteria. These types include *Haemophilus influenzae*, Streptococcus species including *pneumoniae* (particularly serotypes 1, 4, 5, 6A, 6B, 9V, 14, 18C, 19F and 23F) *pyogenes* and *agalactiae, Neisseria meningitidis* (such as serogroup a, b and c), *Klebsiella pneumoniae, Pseudomonas aeruginosa* and *Staphylococcus aureus.*

Non-bacterial polymers can be derived from yeast and fungi, for example, *Cryptococcus neoformans*, or carbohydrate containing units found uniquely on cancer cells or those found associated with allergens.

The conjugates of this invention can be prepared by any of the biologically compatible methods known in the art for coupling of carbohydrate containing antigens or other antigens to carriers. The method of coupling is most preferably covalent coupling whereby the carbohydrate containing antigen or other antigens is bound directly to the cytokine, lymphokine, hormone or growth factor. However, other means by which the antigen is conjugated to the cytokine, lymphokine, hormone or growth factor is included within the scope of the invention. Many such methods are currently available for coupling of carbohydrate containing antigens or other antigens to carriers. Most methods create either amine or amide bonds, or in some cases thio-esters. One particularly preferred method for coupling a carbohydrate containing antigen to the cytokine, lymphokine, hormone or growth factor is by reductive amination which has been described by Anderson, P. W., U.S. Pat. No.. 4,673,573, issued Jun. 16, 1987, and U.S. Pat. No. 4,761,283, issued Aug. 2, 1988, the teachings of which are incorporated herein by reference.

The conjugates of this invention can be used to elicit an immune response to an antigen, such as a carbohydrate containing antigen or saccharide, in a warm-blooded animal. The method comprises administering to the animal, an immunologically effective dose of a conjugate comprising a carbohydrate containing antigem bound to a cytokine, lymphokine, hormone or growth factor in a vaccine composition. The vaccine compositions are useful for the prevention of microbial infections. The conjugates may be administered in a pharmaceutically acceptable vehicle, such as physiological saline, or ethanol polyols (such as glycerol or propylene glycol). The vaccine composition may optionally comprise adjuvants, such as vegetable oils or emulsions thereof, surface active substances, e.g., hexadecylamine, octadecyl amino acid esters, octadecylamine, lysolecithin, dimethyl-dioctadecylammonium bromide, N,N-dicoctadecyl-N'-N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes (ISCOMS); oil emulsions; and mineral gels. The conjugates of this invention may also be incorporated into liposomes or ISCOMS. Supplementary active ingredients may also be employed. The conjugate can also be adsorbed onto a mineral suspension, such as alum, i.e., aluminum hydroxide or aluminum phosphate to further modulate the protective immune response to the carbohydrate containing antigen.

The vaccines can be administered to a human or animal in a variety of ways. These include intradermal, transdermal (such as by slow release polymers), intramuscular, intraperitoneal, intravenous, subcutaneous, oral and intranasal routes of administration. The amount of conjugate employed in such a vaccine will vary depending upon the identity of the carbohydrate containing antigen or other antigen employed. Adjustment and manipulation of established dosage ranges used with traditional carrier conjugates for adaptation to the present conjugate vaccines is well within the ability of those skilled in the art. The conjugates of the present invention are intended for use in the treatment of both immature and adult warm-blooded animals, and in particular humans. Also, the use of the present methods and conjugates is not limited to prophylactic applications; therapeutic applications are also contemplated (e.g., AIDS prophylaxis and therapy), as well as immune focusing to alter growth, productivity or reproduction.

A vaccine composition which can be useful in the vaccination against meningitis caused by *Haemophilus influenzae* will comprise the oligomer polyribosyl-ribitolphosphate (PRP) of *Haemophilus influenzae* type b conjugated to interleukin-2. Bacterial meningitis in the United States is most commonly caused by *H. influenzae* type b.

The immunogenic conjugates of the invention can be admixed with an antigenic determinant, or antigen from the same or different organism in a pharmaceutically acceptable vehicle and an optional adjuvant to produce a co-vaccine which can be used to elicit an immune response to both the conjugated antigen and the admixed nonconjugated antigen.

Suitable antigens which can be used in the covaccine compositions of the invention include particulate antigens, such as those derived from bacteria, viruses, parasites or fungi and microcomponents of cells and soluble antigens, such as proteins, peptides, hormones and glycoproteins. Antigens of particular interest are viral, fungal, parasite or bacterial antigens, allergens, autoimmunity related antigens, or tumor-associated antigens. The antigens can be obtained from natural sources or they can be produced by recombinant DNA technology or by other artificial means.

Among the bacterial antigens of interest are those associated with the human bacterial pathogens including, but not limited to for example, typable and nontypable *Haemophilus influenzae, Escherichia coli, Neisseria meningitidis, Streptococcus pneumoniae, Streptococcus pyogenes, Branhamella catarrhalis, Vibrio cholerae, Corynebacteria diphtheriae, Neisseria gonorrhoeae, Bordetella pertussis, Pseudomonas aeruginosa, Staphylococcus aureus, Klebsiella pneumoniae* and *Clostridium tetani*. Some specific bacterial antigens include bacterial surface and outer membrane proteins (e.g. from *Haemophilus influenzae, Neisseria meningitidis, Neisseria gonorrhoeae* or *Branhamella catarrhalis*) and bacterial surface proteins (e.g. the M protein from *Streptococcus pyogenes.*).

Viral antigens from pathogenic viruses include but are not limited to, human immunodeficiency virus (types I and II), human T-cell leukemia virus (types I, II and III), respiratory syncytial virus, hepatitis A, hepatitis B, hepatitis C, non-A and non-B hepatitis virus, herpes simplex virus (types I and II), cytomegalovirus, influenza virus, parainfluenza virus, poliovirus, rotavirus, coronavirus, rubella virus, measles virus, varicella, Epstein Barr virus, adenovirus, papilloma virus and yellow fever virus.

Several specific viral antigens of these pathogenic viruses include the F protein (especially antigens containing the F peptide 283-315, described in WO89/02935 entitled "Respiratory Syncytial Virus: Vaccines and Diagnostic Assays" by Paradiso, P. et al.) and the N and G proteins of respiratory syncytial virus (RSV), VP4 (previously known as VP3), VP6 and VP7 polypeptides of rotavirus, envelope glycoproteins of human immunodeficiency virus and the surface and presurface antigens of hepatitis B and herpes glycoproteins B and D.

Fungal antigen that can be those derived from fungi including but are not limited to Candida spp. (especially *albicans*), Cryptococcus spp. (especially *neoformans*), Blastomyces spp. (e.g., *dermatitidis*), Histoplasma spp. (especially *capsulatum*), Coccidroides spp. (especially *immitis*), Paracoccidroides spp. (especially *brasiliensis*) and Aspergillus spp. Examples of parasite antigens include but are not limited to Plasmodium spp., Eimeria spp., Schistosoma spp., Trypanosoma spp., Babesia spp., Leishmania spp., Cryptosporidia spp., Toxoplasma spp. and Pneumocystis spp.

Also of interest are various antigens associated with auto-immune diseases, such as rheumatoid arthritis and lupus erythematosus.

The modulation of the immune response has a number of important implications. For example, the adjuvant action of the cytokine, lymphokine, hormone or growth factor can increase the concentration of protective antibodies produced against the antigenic portion of the conjugate in the vaccinated organism. Likewise, antibody production against antigens co-administered with the conjugate can be increased. As a result, effective (i.e., protective) vaccination can be achieved with a smaller quantity of conjugated antigen and/or co-administered antigen than would be normally required. This reduction in the required amount of conjugated antigen and co-administered antigen may lead to more widespread use of vaccines which are difficult or costly to prepare or which are weakly immunogenic. This is especially true in the developing nations which must face such epidemics as malaria and cholera, with very limited health care budgets. It may also provide for safer vaccination which the antigen is toxic at the concentration normally required for effective immunization. By reducing the amount of antigen, the risk of toxic reaction is reduced.

Other applications may also include the elicitation of an immune response to stimulate or inhibit the stability or interaction of cellular modifiers, including hormones with their corresponding receptors or binding components. In this fashion, the immune response can be used to inhibit/enhance growth, reproduction, differentiation, and overall performance. Alternatively, the quality of the immune response can be manipulated to optimize the desired protective response.

In a specific embodiment of this invention, IL-2-conjugates have an added advantage; the binding of the carbohydrate containing antigen or other antigen to specific B and T cells focuses the IL-2 into the vicinity of the B and T cell interleukin receptors.

Cytokines, lymphokines, hormones and growth factors by means of their immunomodulating activity, can help evoke a protective immune response against marginally or non-immunogenic conjugated antigens and bound nonconjugated antigens. In this manner, vaccine composition containing fragments of larger proteins, synthetic antigens or products of recombinant DNA technology may be made more potent by mixture with conjugates of the present invention.

Typically, vaccination regimens call for the administration of antigen over a period of weeks or months in order to stimulate a "protective" immune response. A protective immune response, is an immune response sufficient to protect the immunized organism from productive infection by a particular pathogen or pathogens to which the vaccine is directed. Carbohydrate containing antigens or other antigens, when conjugated to a cytokine, lymphokine, hormone or growth factor and optionally co-administered with antigen from the same or different organism, can modify the generation of a protective immune response. This may reduce the time course of effective vaccination regimens. Further, vaccine formulations comprising the immunogenic conjugates of this invention are stable for a period of time sufficient to allow the manufacture, shipment and storage of the vaccine formulations.

It is to be understood from the above discussion, that the use of the term antigen is meant to imply either the whole antigen or one of its determinants, and is also meant to encompass hapten molecules which could benefit by an increase in the immune response due to the presence of the conjugates of the present invention. The foregoing list of antigens is for exemplary purposes only. Additional antigens which can be used in the co-vaccine compositions of the present invention are readily ascertained by one skilled in the art.

The invention is further illustrated by the following non-limiting Examples:

EXAMPLE 1

PRP-rhIL-2 Conjugates

Recombinant human rhIL-2 (1 mg freeze-dried, Cetus, Emeryville, Calif.) was reconstituted with 300 µL of distilled water and divided into 100 µL aliquots. Each 100 µL aliquot contained 333 µg of rhIL-2.

Oligosaccharide of PRP (degree of polymerization 20: Dp 20) was coupled onto rhIL-2 at 2:1 or 20:1 weight ratio of PRP to rhIL-2 (in the starting reaction) by reductive amination (Anderson, P. W., U.S. Pat. No. 4,673,574, issued Jun. 16, 1987, and U.S. Pat. No. 4,761,283, issued Aug. 2, 1988) according the following three reaction conditions:

Reaction 1

In the first reaction, 100 µL of rhIL-2 was mixed with 2 M bicarbonate buffer pH 9. 5 (5 µL) which brought the reaction mixture to pH 8.5. Sodium cyanoborohydride (57 mg/mL in deionized water, 2 µL) was added and the solution stored at 30° C. for 24 hours.

Reaction 2 rhIL-2 (1.00 µL, 333 µg) was mixed with freeze-dried PRP of Haemophilus influenzae type b oligosaccharide (HbO) (WW-2-65, 600 µg). Sodium bicarbonate buffer 2 M pH 9.2 (5 µL) was added to make the reaction mixture pH 8.5. Sodium cyanoborohydride (57 mg/mL in deionized water, 2 µL) was added and the solution stored at 37° C. for 24 hours.

Reaction 3 rhIL-2 (100 µL, 333 µg) was mixed with freeze-dried HbO (WW-2-65, 6.0 mg). Sodium bicarbonate buffer 2 M pH 9.2 (5 µL) was added to make the reaction mixture pH 8.5. Sodium cyanoborohydride (57 mg/mL in deionized water, 20 µL) was added and the solution stored at 37° C. for 24 hours.

After 24 hours, each of the reaction mixtures were dialyzed against several changes of saline using an 8,000 MW membrane to remove inorganic ions, such as cyanide. HPLC analysis of the crude reaction mixture on an Ultrahydrogel (Waters, Milford, Mass.) columns 125/250 in phosphate buffer showed an increase in size of the protein component (conjugated rhIL-2), as compared to the unconjugated rhIL-2 (FIG. 1).

Figure 2:
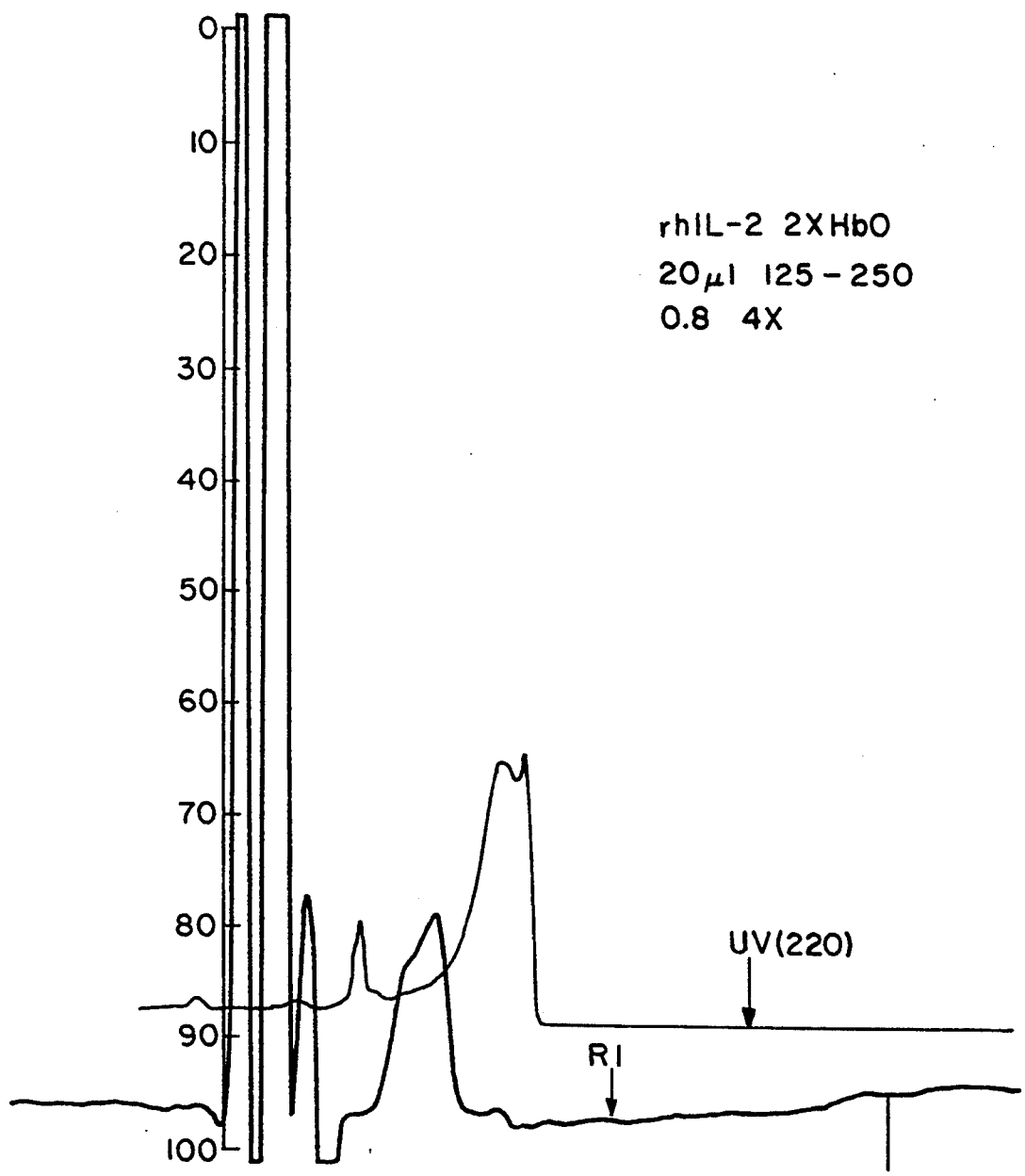
FIG. 2 shows a chromatogram of a PRP-rhIL-2 conjugate in a 2:1 (w/w) ratio of PRP to rhIL-2 in the starting reaction.
Figure 3:
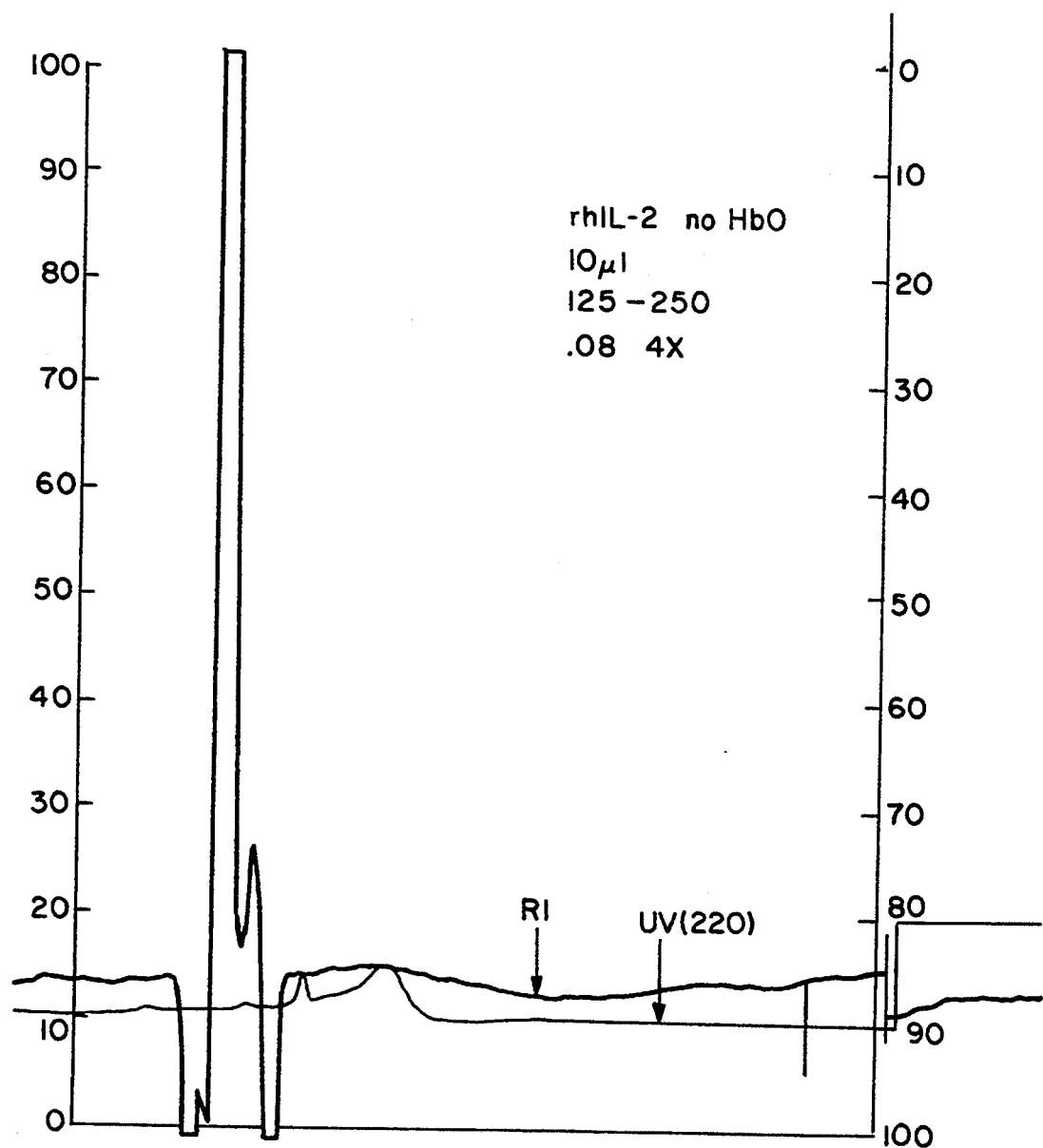
FIG. 3 shows a chromatogram of a mock conjugate of rhIL-2, wherein the conjugation procedure was followed without added PRP.

FIG. 1 shows an HPLC chromatogram of the crude conjugate mixture of PRP-rhIL-2 in a 20 to 1 ratio of PRP to rhIL-2. The mixture was analyzed on ultrahydrogel column in phosphate buffered saline. FIGS. 2 and 3 show HPLC chromatograms for PRP-rhIL-2 conjugate in a 2 to 1 ratio of PRP to rhIL-2 and for mock conjugates, respectively.

Figures 4, 5A:
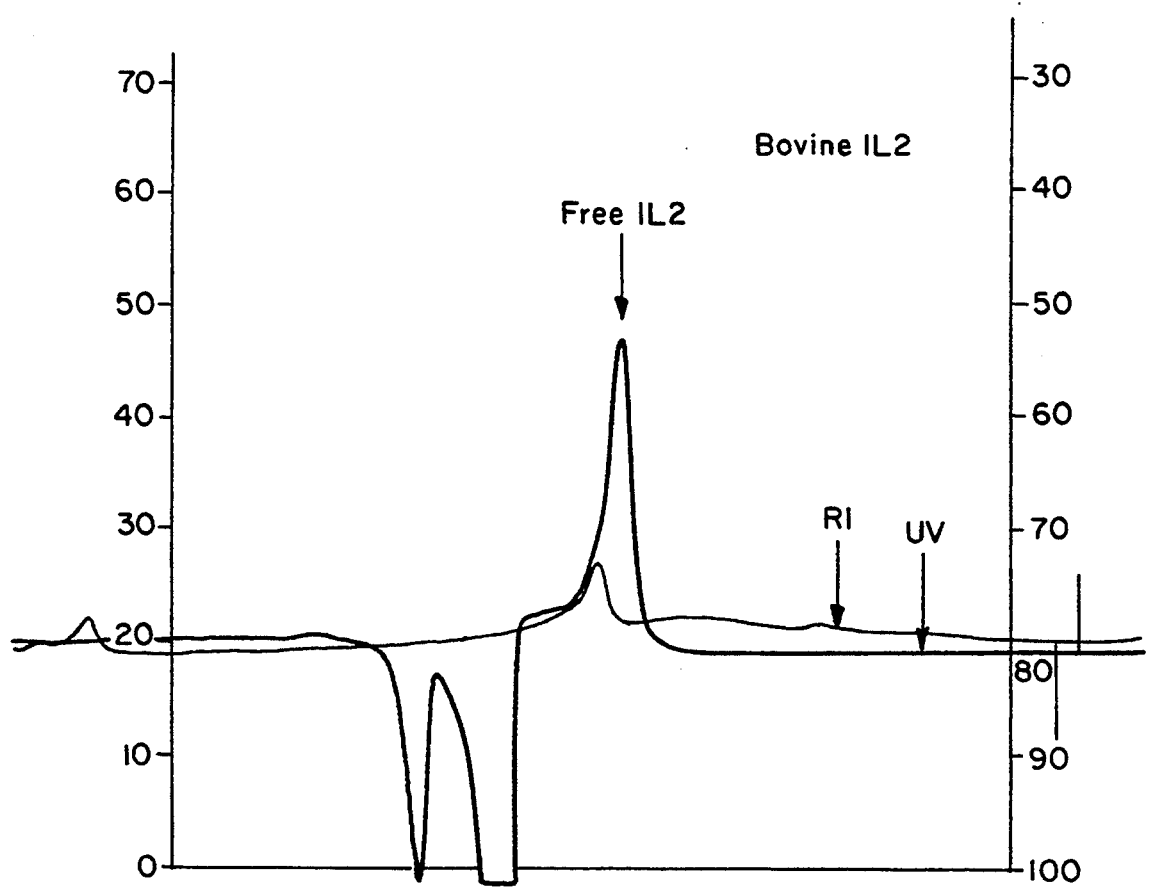
FIG. 4 shows an immunoblot of selected conjugates which were detected with monoclonal antibodies to PRP. From left to right, the lanes contain PRP-CRM, rhIL-2, PRP, PRP-rhIL-2(2X), PRP-rhIL-2(2X), Blank, PRP-rhIL-2(20X), and PRP-rhIL-2(20X).
FIG. 5a-c show HPLC analyses of (a) unconjugated recombinant bovine IL-2 (BrIL-2), (b) PRP-BrIL-2 (2:1) conjugate and (c) PRP-BrIL-2 (20:1) conjugate.

Crude conjugates were then tested by dot blot analysis for coupling of PRP to rhIL-2 using mouse monoclonal anti-PRP antibody (El17-5; Lab Services, Praxis Bioiogics Inc Rochester N.Y.) One or two µL of the conjugates was applied on a nitrocellulose paper and air dried for 10 minutes at room temperature. The paper was blocked with BLOTTO (5% non-fat dry milk in 10 mM sodium phosphate buffered saline pH 7.2, 150 mM NaCl). The blot was reacted with monoclonal anti-PRP antibodies. Following extensive washings with BLOTTO, blots were reacted with HRP-goat anti-mouse antibodies. The blots were developed with a solution containing 0.01% hydrogen peroxide; 0.06% 4-chloro-1-napthol (Sigma Chemical Co., St. Louis, Mo.). rhIL-2 or PRP alone did not show any reactivity and PRP-rhIL-2 conjugate showed positive reactivity. Since PRP alone does not bind to nitrocellulose, the data suggests that PRP is coupled to rhIL-2 (FIG. 4).

Biological Activity

Conjugates were stored at 4° C. and various days thereafter, rhIL-2 activity was monitored in a biological assay using CTLL cell line obtained from the ATCC. CTLL is a rhIL-2 dependent cell line and the deprivation of rhIL-2 from these cells results in the death of these cells. Briefly, $5 \times 10^3$ CTLL cells were cultured with various concentrations of rhIL-2 or PRP-rhIL-2. The growth of CTLL was monitored by the incorporation of [$^3$H]-thymidine (Table I).

Table I shows the biological activity of interleukin-2 in various PRP-rhIL-2 conjugates. rhIL-2 and conjugates were titrated at various concentrations into the cultures containing $3 \times 10^3$ CTLL cells. The growth of cells was measured by the incorporation of [$^3$H]thymidine. Data are presented as % control response. The stimulation indices are normalized to the values obtained with a standard preparation of rhIL-2. From the data, PRP-rhIL-2 (20X) possess better rhIL-2 activity than PRP-rhIL-2 (2X) or mock rhIL-2 conjugates.

TABLE I

STABILITY OF PRP-rhIL-2 CONJUGATE VACCINE
STIMULATION INDEX (Expressed as % Control Response)
Days After The Conjugation Reaction

| Stimulator | 10 | 20 | 40 | 50 | 70 |
|---|---|---|---|---|---|
| Mock conjugate | 37 | 1.5 | 2.5 | 18 | 8 |
| PRP-rhIL-2 (2:1) | 33 | 4.9 | 61 | 40 | 17 |
| PRP-rhIL-2 (20:1) | 68 | 23 | 86 | 91 | 95 |
| PRP-CRM$_{197}$ (HbOC) | 0 | 0 | 0 | 0 | 0 |

Immunogenicity of PRP-rhIL-2 conjugate vaccines

Swiss-Webster mice (Taconic Farms, Germantown, N.Y.) were immunized with PRP-rhIL-2 (20:1) or PRP-rhIL-2 (2:1) conjugate vaccines. Each vaccine was tested in a group of 5 animals. PRP-CRM197 conjugate vaccines (HbOC, Praxis Biologics, Inc., Rochester, N.Y.) were used as positive control. PRP-rhIL-2 conjugate vaccines (stored for 135 days at 4° C.) were injected intramuscularly into mice in an amount of 10 or 1 μg of rhIL-2 without the use of adjuvant. PRP-CRM197 was used at 1 μg of PRP per mouse. The mice were then boosted at two weeks using the same dose and route of injection. Serum samples were taken at 0, 2 and 4 weeks, pooled and used to determine antibody response to PRP by Farr assay according to the following procedure:

Antibody to PRP was determined by a standardized Farr radioimmunoassay. Various dilutions of sera, sera standard and assay controls were prepared in fetal bovine sera and 25 μl aliquots transferred, in duplicate, to 1.5 ml Eppendorf tubes. [$^3$H]-PRP (50 μl) with [$^{36}$Cl]-tracer was added to all tubes. The samples were vortexed and incubated overnight at 4° C. Saturated ammonium sulfate (75 μl) was added to all samples after which the samples were vortexed and incubated at 4° C. for 40 min. The supernatant was carefully aspirated and 400 μl of distilled water was added to all pellets. After vortexing, the entire contents of the vial and the vial itself were placed in a scintillation vial containing 10 ml of scintillation fluid. After vigorous agitation, the vials are counted on a liquid scintillation counter. The concentration of antibody bound to PRP was calculated, in comparison to a known standard.

Table II shows the anti-PRP antibody response elicited in mice immunized with various conjugate vaccines. A primary anti-PRP antibody response varying from 2 to 3.5 μg was observed with different vaccines. A boostable response was observed with most of the vaccines on week 4 PRP-rhIL-2 (20:1) induced a response which is comparable to that of *Haemophilus influenza* type b oligosaccharide CRM$_{197}$ conjugate (HbOC).

TABLE II

Anti-PRP Antibody Response to PRP-rhIL-2 Conjugate Vaccines

| Vaccines | dose (μg) | Anti-PRP antibody (μg/ml)* | | |
|---|---|---|---|---|
| | | Wk 0 | Wk 2 | Wk 4 |
| PRP-rhIL-2 (20:1) | 10 | 0.17 | 2.0 | 8.0 |
| PRP-rhIL-2 (20:1) | 1 | 0.10 | 2.0 | 5.37 |
| PRP-rhIL-2 (2:1) | 10 | 0.10 | 3.54 | 4.19 |
| PRP-rhIL-2 (2:1) | 1 | 0.14 | 2.0 | 4.20 |
| HbOC | 1 | 0.10 | 2.0 | 8.71 |

PRP-rhIL-2 conjugate vaccines were injected based on rhIL-2 concentration and HbOC was used based on PRP concentration.
*Data from previous experiments show that PRP(DP20) alone or PRP mixed with protein do not induce any PRP antibody response.

EXAMPLE 2

PRP-BrIL-2 Conjugates

It is possible that the induction of anti-PRP antibody in mice by PRP-rhIL-2 vaccine may be due to the carrier effect of the IL-2, rather than the targeting of PRP to the appropriate B cells. In order to rule out this possibility, this hypothesis was tested in a homologous system. To exemplify this phenomenon, PRP was coralcurly coupled to recombinant bovine IL-2 (BrIL-2) and this conjugate was tested for immunogenicity in a bovine system.

Figure 5B:
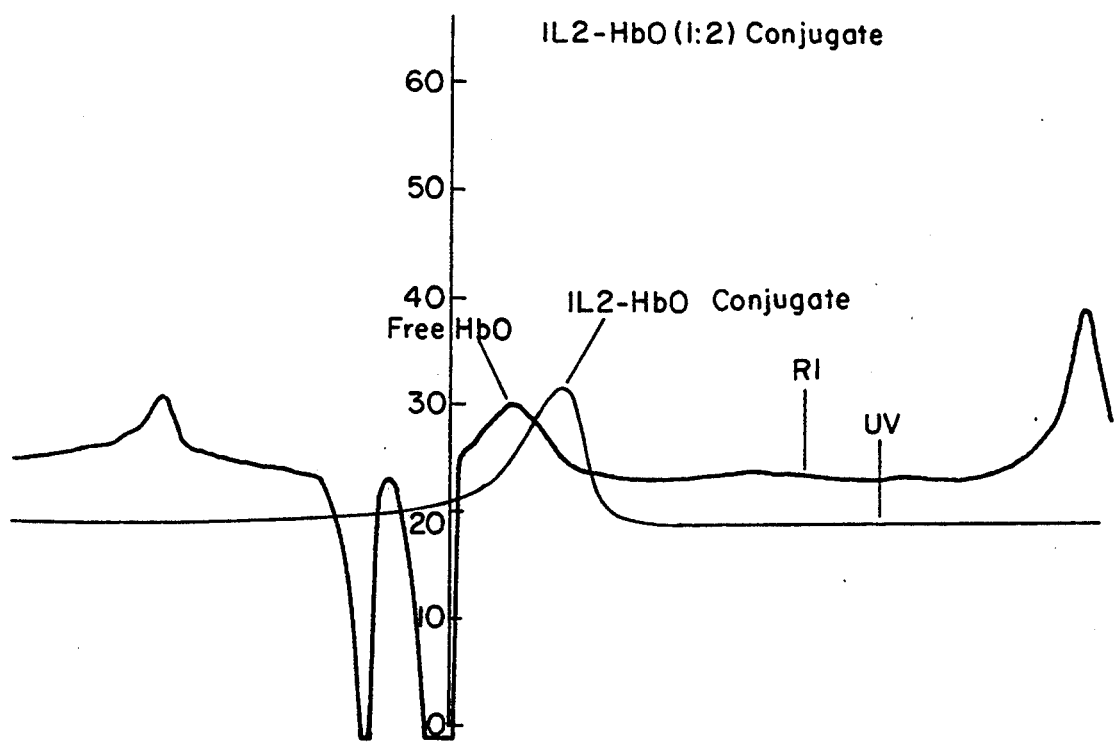
Figure 5C:
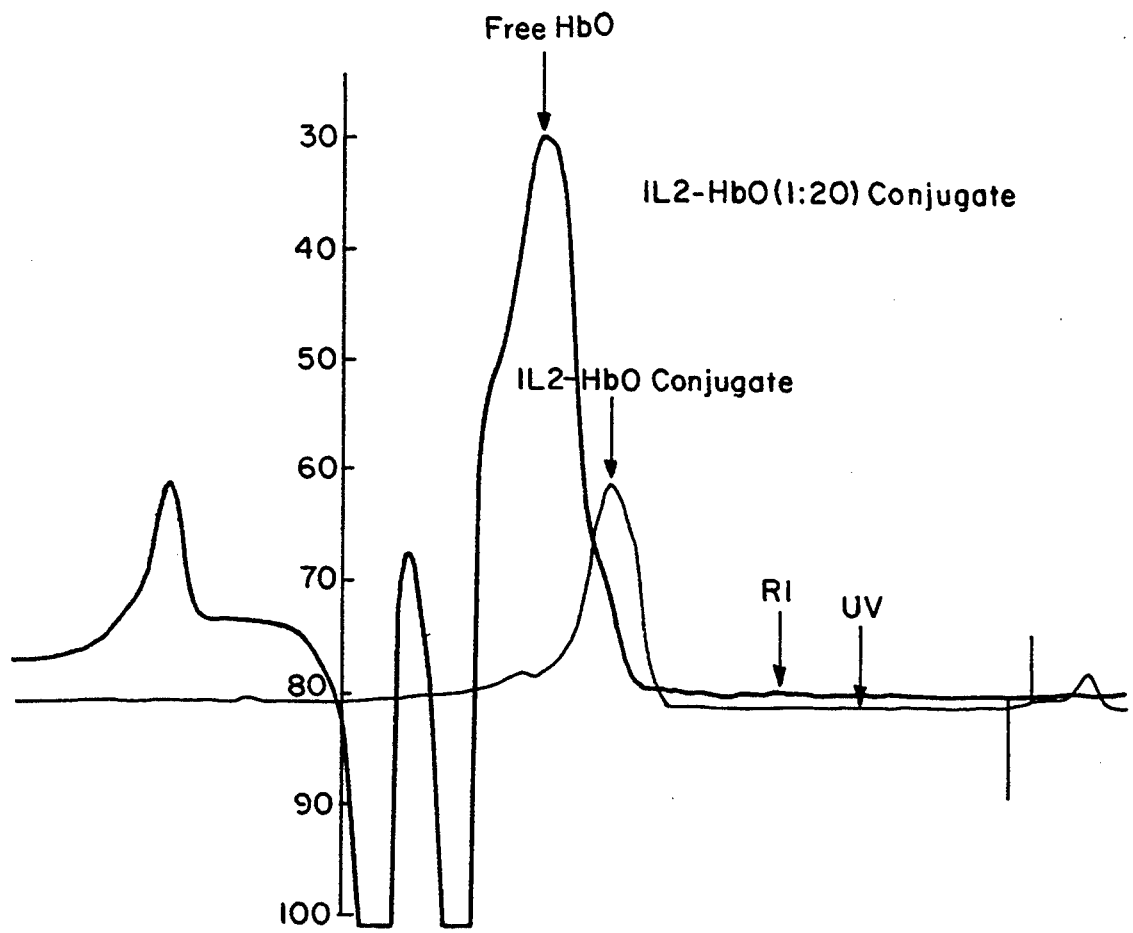

PRP was coupled to recombinant bovine IL-2 at 2:1 and 20:1 (PRP:IL-2) ratio following the protocol described in Example 1. After 24 hours, conjugates were dialyzed against several changes of saline using an 8,000 MW membrane to remove inorganic ions such as cyanide. The crude mixtures were analyzed by HPLC using Ultrahydrogel (Waters, Milford, Mass.) columns 125/250 in phosphate buffer. An increase in the size of the protein component as compared to the unconjugated BrIL-2 suggests a good conjugation (FIG. 5).

Purified conjugates and unconjugated BrIL-2 were evaluated in SDS-PAGE and Western blot. Materials were dissolved in 100 μl of a sample buffer (0.2M Tris buffer 2-methanol and 20% glycerol) and heated for 5 min. at 100° C. Analyses were performed using the Bio-Rad mini protein gel system (Redmond, Calif.). Gels were 1.5 mm thick and the separating gel contained 15% acrylamide with an acrylamide to bis ratio of 30:0.8 (0.37M Tris-HCl, pH 8.8 and 0.1% SDS). The stacking gel contained 4.8% acrylamide with the same ratio of acrylamide to his.

Ten to fifteen microliters containing 1–10 μg of samples were applied to each lane. Following electrophoresis, gels were stained for at least one hour with 0.125% Coomassie blue in ethanol:acetic acid:water (5:1:5), then desrained with the same solvent system without the dye. Pre-stained molecular weight standards were used to assist in the determination of the relative molecular weight of protein. Duplicate gel without staining was used for Western blot analysis. The major band of approximately 16,000 dalton molecular weight was observed in the lane loaded with BrIL-2 alone. The conjugates appear as diffused band at the higher molecular weight region. No evidence of unconjugated BrIL-2 was observed.

Samples separated on PAGE were transferred electrophoretically onto nitrocellulose membranes at 0.45 mAmps for 90 minutes in 25 mM Tris-383 mM glycine pH 8.8 room temperature. Membranes were soaked in BLOTTO (5% non-fat dry milk in phosphate buffered saline) at 37° C. for 1 hour. Membranes were probed with a predetermined concentration of a monoclonal anti-PRP antibody (E117-5) or a polyclonal rabbit anti-BrIL-2 for 1 hour at 37° C. and washed with BLOTTO.

Figure 6:
FIG. 6 shows a Western blot analysis of PRP-BrIL-2 vaccine. The blot was developed with a monoclonal anti-PRP antibody (E117-5) or with a polyclonal anti-BrIL-2 antibody as indicated.

Bound antibodies were detected with horseradish peroxidase conjugated secondary antibody (Kirkegaard and Perry, MD) in BLOTTO for 1 hour at 37° C. Blots were washed 3-4X with PBS and developed with PBS containing 0.01% hydrogen peroxide; 0.06% 4-chloro-1-naphthal in methanol for 20 minutes at room temperature. The reaction was stopped by transferring the filters to distilled water and the filters dried by blotting. The data is presented in FIG. 6. Anti-PRP antibody reacted with both PRP-BrIL-2 conjugates but did not react with the unconjugated BrIL-2. Molecular weight of the conjugates also increased considerably. Free PRP, when not coupled to any protein, do not adhere to the nitrocellulose membrane, The data suggests that PRP was covalently coupled to BrIL-2.

Anti-BrIL-2 reacted with free IL-2 and IL-2 conjugates. The data is similar to that observed with anti-PRP antibody.

Covalent coupling of PRP onto the IL-2 has been confirmed by amino acid analysis. As saccharides are coupled to the epsilon amino group of lysine residue of the protein, a reduction of lysine and generation of an unique hydroxyethyl lysine residue was monitored. The analysis of the data shows hydroxyethyl lysine demonstrating the covalent coupling of PRP onto the protein.

Biological Activity

Figure 7:
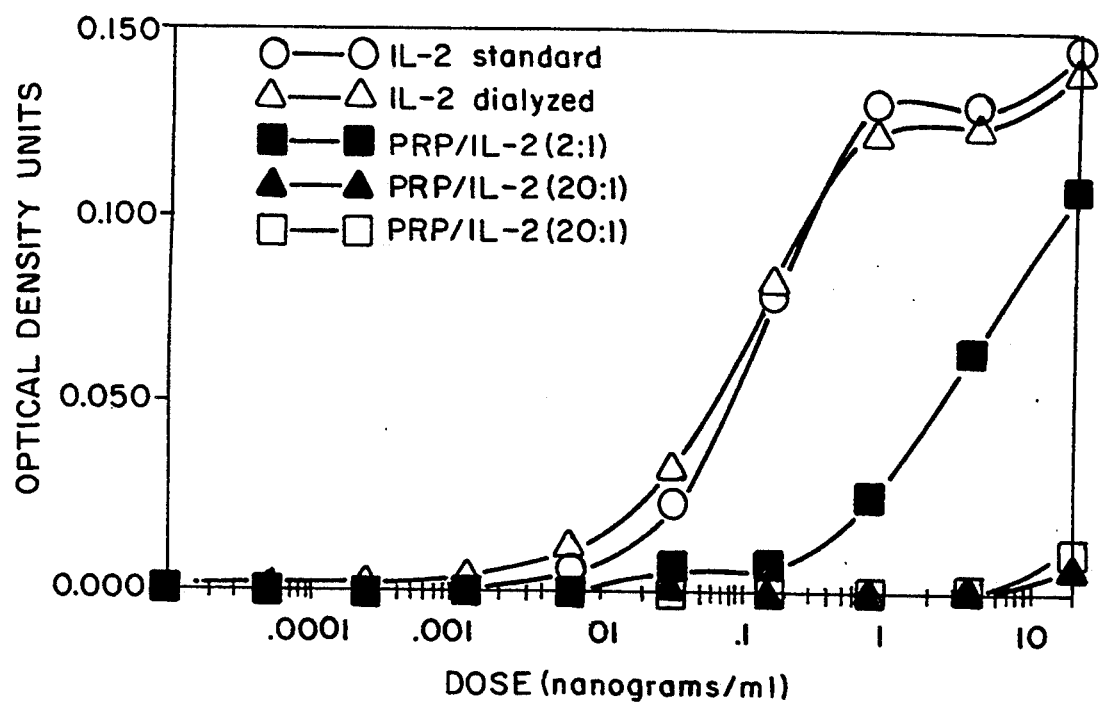
FIG. 7 shows a comparison of the biological activities of BrIL-2 with the PRP-BrIL-2 conjugates in a BT-2 bioassay.

Conjugates were stored at 4° C. and the biological activity of the bovine IL-2 was monitored in a bioassay using IL-2 dependent bovine T cell line, BT-2. The deprivation of IL-2 from these cell line results in the death of these cells. Briefly, $5 \times 10^4$ BT-2 cells were cultured in a 96 well flat-bottom microculture plate in the presence of different concentrations of BrIL-2 or PRP-BrIL-2 conjugates. After 48 hours, 10 μl of MTT [3-(4,5-dimethylthiazol-2-yl)-2,5-diphenyl tetrazolium bromide] solution was added (5 mg/ml of PBS) and mixed 20 times. MTT is cleaved by living cells to yield a dark blue formazan product. The formazan product was quantitated by measuring absorbance at 550 nm by addition of isopropanol. The data are presented in FIG. 7. Both 2:1 and 20:1 conjugates retained biological activity which are 100 to 1000 times lower respectively than the unconjugated BrIL-2.

Immunogenicity of PRP-BrIL-2 Conjugate Vaccine

Groups of 3 cows were immunized with the conjugate vaccine. PRP-CRM197 (HbOC) conjugate vaccines were used as a positive control and PRP mixed with BrIL-2 was used as a negative control. All vaccines were formulated in aluminum phosphate at a concentration of 1 mg/ml. Each animal received 10 μg of PRP/dose. Cows were pre-bled to estimate the pre-existing antibody level to PRP and those with high anti-PRP titers were distributed equally between experimental and control groups.

Animals were immunized subcutaneously with 10 μg of PRP or conjugates in 2 ml volume on week 0 and bled on weeks 1 and 2. A second dose of vaccine was administered on week 2 and blood was collected on weeks 3 and 4. Antibody response to PRP was measured by a standardized Fart radioimmunoassay as previously described. Geometric mean anti-PRP antibody titers are presented in Table III. PRP-IL-2 (2:1) conjugate induced anti-PRP antibodies at week 3 which are 2.3 fold higher than the preimmune antibody level and the PRP-IL-2 (20:1) induced an approximately 3 fold increase in antibodies at week 3. HbOC, human PRP-CRM197 vaccine formulation, induced a six fold increase in anti-PRP titer at week 3. PRP when mixed with BrIL-2 did not induce a significant rise in the anti-PRP antibody level. The data suggest that the RPP-IL-2 (2:1) and (20:1) conjugates target the vaccine onto the appropriate lymphocytes to stimulate the response.

TABLE III

Bovine Anti-PRP Antibody Response to PRP-BrIL-2 Conjugates

| Anitgens | GMT Anti-PRP Antibody (μg/ml) | | | | Fold Increase* |
|---|---|---|---|---|---|
| | Wk 0 | Wk 1 | Wk 2 | Wk 3 | |
| PRP + IL-2 | 0.70 | 0.46 | 0.54 | .46 | none |
| PRP-CRM197 (HbOC) | 0.38 | 0.38 | 0.98 | 2.3 | 6.1 |
| PRP-IL-2 (20:1) | 0.35 | 0.48 | 0.55 | 1.0 | 2.8 |
| PRP-IL-2 (2:1) | 0.31 | 0.35 | 0.36 | .71 | 2.3 |

*Fold increase at week 3 is expressed as increase over the week 0 antibody titer.

Equivalents

Those skilled in the art will recognize, or be able to ascertain using no more than routine experimentation, many equivalents to the specific embodiments of the invention described specifically herein. Such equivalents are intended to be encompassed in the scope of the following claims:

We claim:

1. An immunogenic conjugate comprising a bacterial capsular polymer bound to a lymphokine selected from the group consisting of interferon, interleukin 1α, interleukin-2β and interleukin-2.

2. The conjugate of claim 1, wherein the polymer is covalently bound to the lymphokine.

3. The conjugate of claim 2, wherein the polymer is bound to the lymphokine by reductive amination.

4. The conjugate of claim 1, wherein the polymer fragment is derived from *Haemophilus influenzae, Escherichia coli, Neisseria meningitidis, Streptococcus pneumoniae, Streptococcus pyogenes, Branhamella catarrhalis, Vibrio cholerae, Corynebacteria diphtheriae, Neisseria gonorrhoeae, Bordetella pertussis, Pseudomonas aeruginosa, Staphylococcus aureus, Klebsiella pneumoniae* and *Clostridium tetani.*

5. The conjugate of claim 4, wherein the polymer is polyribosylribitolphosphate.

6. The conjugate of claim 4, wherein the fragment or oligomer is derived from *Streptococcus pneumoniae.*

7. The conjugate of claim 6, wherein the fragment or oligomer is from serotype 1, 4, 5, 6A, 6B, 9V, 14, 18C, 19F or 23F of *S. pneumoniae.*

8. The conjugate of claim 1, wherein the fragment or oligomer is from group A or group C capsular saccharide of *N. meningitidis.*

9. A vaccine composition, comprising an immunogenic conjugate, comprising a bacterial capsular polymer bound to a lymphokine selected from the group consisting of interferon, interleukin-1α, interleukin-1β and interleukin-2, in a pharmaceutically acceptable vehicle and an optional adjuvant.

10. The vaccine composition of claim 9, wherein the polymer is derived from *Haemophilus influenzae, Escherichia coli, Neisseria meningitidis, Streptococcus pneumoniae, Streptococcus pyogenes, Branhamella catarrhalis, Vibrio cholerae, Corynebacteria diphtheriae, Neisseria gonorrhoeae, Bordetella pertussis, Pseudomonas aerugi-*

*nosa, Staphylococcus aureus, Klebsiella pneumoniae* and *Clostridium tetani.*

11. The vaccine composition of claim 9, wherein the polymer is polyribosylribitolphosphate.

12. The vaccine composition of claim 10, wherein the polymer is derived from *Streptococcus pneumoniae.*

13. The vaccine composition of claim 12, wherein the polymer is from serotype 1, 4, 5, 6A, 6B , 9V, 14, 18C, 19F or 23 F of *S. pneumoniae.*

14. The vaccine composition of claim 10, wherein the polymer is from group A or group C capsular saccharide of *N. meningitidis.*

15. The vaccine composition of claim 9, which comprises a mineral suspension of alum as adjuvant.

16. An immunogenic conjugate comprising polyribosylribitolphosphate bound to interleukin-2, wherein interleukin-2 is capable of modifying the immunogenic activity of polyribosylribitolphosphate.

17. A vaccine composition comprising an immunogenic conjugate comprising polyribosylribitolphosphate bound to interleukin-2, wherein interleukin-2 is capable of modifying the immunogenic activity of polyribosylribitolphosphate, in a pharmaceutically acceptable vehicle and an optional adjuvant.

* * * * *